United States Patent [19]
Glasser et al.

[11] Patent Number: 5,802,138
[45] Date of Patent: Sep. 1, 1998

[54] MULTISECTION IMAGING DEVICE

[75] Inventors: Francis Glasser, Eybens; Olivier Peyret, Le Fontanil, both of France

[73] Assignee: Commissariat a l'Energie Atomique, Paris, France

[21] Appl. No.: 792,176

[22] Filed: Jan. 30, 1997

[30] Foreign Application Priority Data

Feb. 29, 1996 [FR] France ................................ 96 02548

[51] Int. Cl.⁶ ............................................. G01T 1/29
[52] U.S. Cl. ................................... 378/98.8; 378/19
[58] Field of Search ........................ 378/98.8, 19.4; 250/370.09, 370.11, 363.02, 363.03, 363.04, 363.05, 363.08, 370.01, 370.08, 370.14

[56] References Cited

U.S. PATENT DOCUMENTS

| | | | |
|---|---|---|---|
| 4,905,265 | 2/1990 | Cox et al. | 378/19 X |
| 4,963,746 | 10/1990 | Morgan et al. | |
| 5,241,576 | 8/1993 | Lonn | 378/19 |
| 5,245,191 | 9/1993 | Barber et al. | |
| 5,291,402 | 3/1994 | Pfoh | |
| 5,319,693 | 6/1994 | Eberhard et al. | 378/19 |
| 5,355,309 | 10/1994 | Eberhard et al. | 378/19 X |
| 5,430,784 | 7/1995 | Ribner et al. | 378/19 X |
| 5,583,903 | 12/1996 | Saito et al. | 378/19 |
| 5,592,523 | 1/1997 | Tuy et al. | 378/19 |

FOREIGN PATENT DOCUMENTS

| | | | |
|---|---|---|---|
| 0 571 135 | 11/1993 | European Pat. Off. | |
| 4-38489 | 2/1992 | Japan | 378/19 |

*Primary Examiner*—David P. Porta
*Attorney, Agent, or Firm*—Burns, Doane, Swecker and Mathis LLP

[57] ABSTRACT

The present invention relates to a multisection imaging device incorporating a source (10) of ionizing radiation (11) and an array of semiconductor detectors (12) able to receive said radiation (11) having traversed a means (14), in which the semiconductor detectors are bidimensional detectors associated with one another in order to obtain several detection rings able to rotate about said means (14), so as to permit the simultaneous acquisition of several imaging sections.

16 Claims, 3 Drawing Sheets

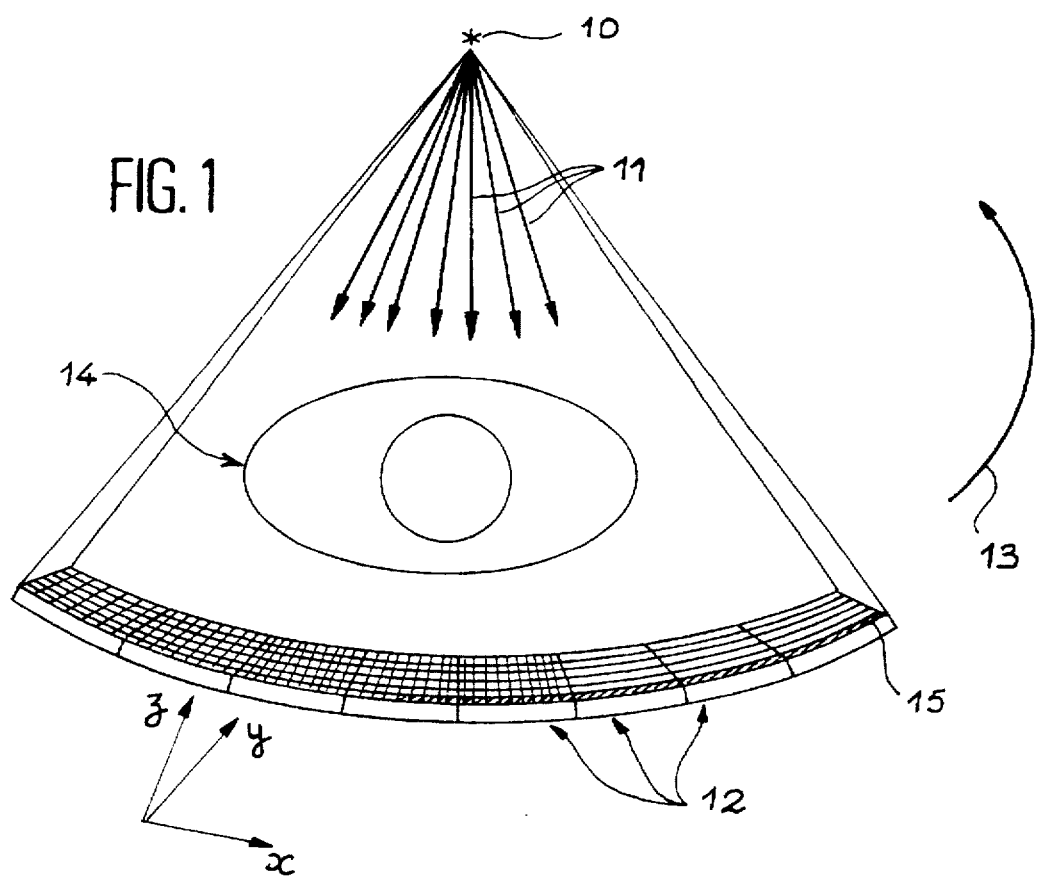
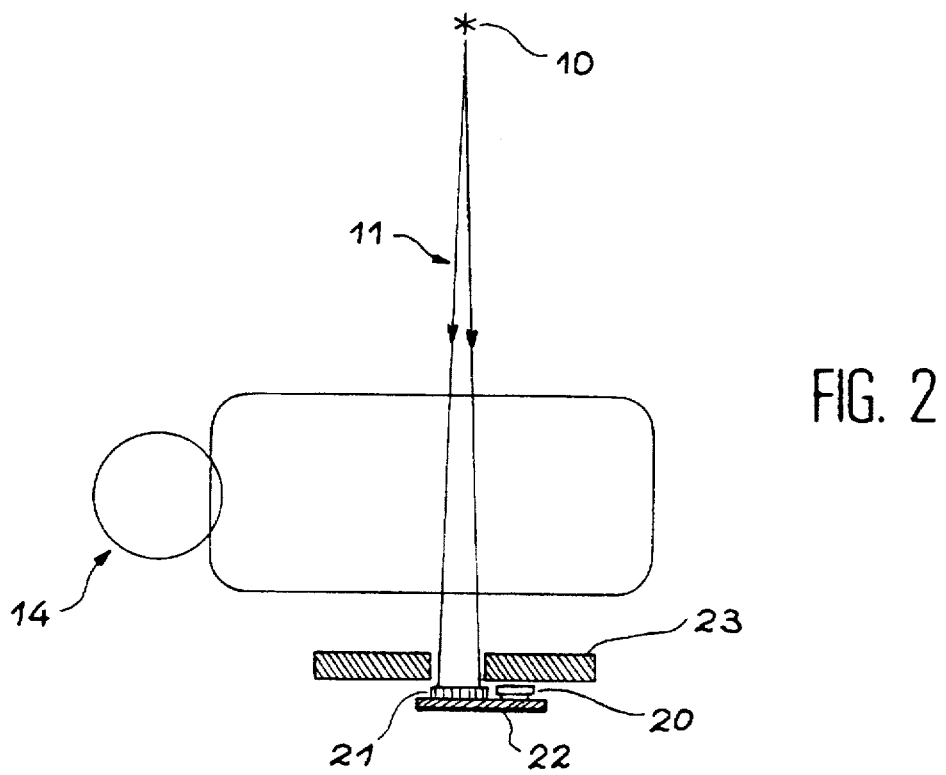

MULTISECTION IMAGING DEVICE

DESCRIPTION

1. Technical Field

The present invention relates to a multisection imaging device. It more particularly applies to imaging devices in X-ray transmission, γ-ray transmission or X-ray emission.

2. Prior Art

The prior art medical X-ray tomography devices use as detectors either gas detectors, or scintillators associated with photodiodes. However, such detectors only effect the acquisition of a single section for each rotation of the source-detector assembly. Volume cartographies are produced by the acquisition of several sections with, for each section, a displacement of the patient perpendicular to the X-ray beam. There is a complete rotation about the patient of the radiation source-detector assembly for each section.

Machines also exist which concatenate the sections by continuously moving the patient. The reconstruction software then takes account of this helical-type acquisition.

Another solution consists of using a bidimensional detector of the radio-logical image intensifier type and acquiring by a complete rotation an array of bidimensional images. The image of the volume is directly reconstructed from these acquisitions, as in the three-dimensional (3D) tomograph described in the article entitled "Development of a 3D CT-Scanner Using Cond Beam" by Masahiro Endo, Nozomu Kamagata, Kazumasa Sato, Yuichi Hattori, Shigeo Kobayaghi, Shin-Ichi Mimuno, Masao Jimbo and Masahiro Kusakabe (SPIE, vol. 2432, pp. 291–297 at the end of the description.

The document entitled "New CT Scanner—Initial Clinical Experience" by C. Becker, U. Fink, M. Seemann and M. Reiser (Electromedica 63; 1995; No. 1) describes a continuous rotation tomograph concatenating the acquisitions.

Several documents describe the use of semiconductor detectors in tomography.

French patent document FR-A-2 432 719, entitled "Radiation Detection Device For Tomography" (March 1979) describes an apparatus for the detection of radiation in the form of pulses having a predetermined duration and comprising a semiconductor detector, which creates an electron charge under the action of the instant radiation, the detector serving to receive at least part of the pulses of the radiations. A signal processing device is coupled in alternating current to the semiconductor detector and forms an electric output signal accurately representing the incident radiation. The signal processing device has a filter only permitting a contribution to the electric output signal of the components, whose frequency is in the predetermined frequency band, which is determined as a function of the duration of the incident pulses, so that the electric output signal has no distortions due to variations in the electrical characteristics within the semiconductor detector. However, the apparatus described in document [3] does not give good results and has not been used since 1979. Thus, there is a problem with regards to the lag of the response of the detector subject to X-radiation.

European patent document EP-A-0 571 135 to Collins, et al., entitled "Hybridized Semiconductor Pixel Detector Arrays For Use In Digital Radiography" (May 1993) describes a semiconductor detector connected to a reading circuit by indium ball for which an application is possible in tomography.

The evolution possibilities of the said detectors are as follows.

For gas detectors, attempts have been made to evolve gas detectors in order to be able to acquire several sections at the same time. However, a solution of this type has not hitherto been adopted. Moreover, the number of sections possible in a configuration of this type remains very small (below 10).

For scintillator detectors associated with photodiodes, the scintillators convert the X-radiation into visible light. This light is measured by photodiodes, which are offset to the side so as not to be damaged by the X-ray beam. Such a structure could evolve in order to produce two or three sections at the same time, but scarcely more than this. In order to obtain a large number of sections with such a detector, it would be necessary to directly couple the scintillator to the photodiodes by means of optical fibres. However, in this case the photodiodes would be susceptable to rapid deterioration.

Thus, in the field of medical imaging, the scanners use gas detectors or scintillator detectors which acquire one or exceptionally two sections for each rotation of the source-detector assembly. In order to acquire a volume information, it is necessary to produce several sections, whose height is fixed at a given examination.

Moreover, the use of scintillator or gas detectors requires conversion means for recovering an electrical information and the detection devices using them are cumbersome as a result. Also for this reason the prior art devices do not permit the alignment of more than two detector arrays.

The use of semiconductor detectors for detecting ionizing radiation within the framework of medical imaging or nondestructive testing, makes it possible to envisage novel functionalities on detection devices, such as the simultaneous acquisition of several sections.

The object of the invention is the use of an array of such detectors for producing a multisection imaging section.

DESCRIPTION OF THE INVENTION

The present invention relates to a multisection imaging device incorporating an ionizing radiation source and an array of semiconductor detectors able to receive said radiation which has traversed an assembly, characterized in that said semiconductor detectors are bidimensional detectors associated with one another so as to produce several detection rings able to rotate about said assembly in order to permit the simultaneous acquisition of several imaging sections. Each elementary semiconductor detector is provided with a blocking contact, which in particular makes it possible to limit the response lag problem of the radiation-exposed detector.

The invention more particularly applies to imaging devices in γ-ray and X-ray transmission and in γ-ray emission.

Advantageously, each bidimensional detector is obtained from high resistivity, elementary semiconductor detectors.

Advantageously, each semiconductor detector is constituted by a material taken from within families of semiconductors of type IV (SiGe), II-VI (ZnS), III-V (GaAs, Inp), and II-VII (HgI2):

CdXTe with e.g. X=Zn or nothing
AsXTe with e.g. X=Alu or nothing
BiXOy with e.g. X=Ge, Si X=12, y=1
PbXO with e.g. X=Ti or nothing
XSe with e.g. X=Cd or nothing Advantageously, the device according to the invention has an electronic measuring circuit, which is offset with respect to the incident beam by means of a connection support. The detectors and reading circuit are connected to said support by metal balls, e.g. based on indium.

3

Advantageously, a reading electronics is connected to the semiconductor detectors by means of a connection support and said electronics is protected from radiation by an absorbing material shield.

Advantageously, each semiconductor detector is formed by a semiconductor plate or chip having on the irradiated face a homogeneous electrode and on the other facing face a plurality of small independent electrodes. As each small electrode defines the size of a detector pixel, it is connected to a metal strip of an interconnection support, e.g. using the metal ball method, e.g. based on indium or conductive rubber. This metal strip is connected to the reading electronics offset to the side by the same method. The examined means can be an object or a subject (patient).

The invention also relates to an imaging process performed by said device, which is characterized in that, on the basis of a single ionizing radiation dose making it possible to bring about an acquisition, the section height can be chose after the acquisition stage at the time of image reconstruction, by summating the contribution of a chosen number of rings, making it possible to select at least one examination volume and/or vary the same.

Advantageously, a first section is given by the reconstruction of images of the response of pixels of the first column of all the planar detectors. At the same time acquisition takes place of the same number of sections as there are columns, the section height being defined by the dimension of the elementary pixel. It can be increased during acquisition by summating the response of several pixels on a section height line.

Thus, according to the invention, the detectors associated with one another make it possible to acquire at the same time several imaging sections. They also allow economies with respect to the radiation tube, so that its life is increased.

The invention also makes it possible to obtain measurements with a fine resolution due to the small spacing between the detectors, in all directions, of approximately 0.1 mm. In the prior art devices, the patient moves relative to the detection ring, so that the resolution in the patient displacement direction is approximately 1 mm. Moreover, the use of semiconductor detectors makes it possible to offset the proximity electronics and protect same against incident radiation.

The device according to the invention can be used in medical tomography, but also for nondestructive testing in industrial tomography. The essential interest is then that it permits a time gain for the testing or inspection of a given volume and for detecting a defective area, e.g. in rocket engine tomography and ceramic tomography.

BRIEF DESCRIPTION OF THE DRAWINGS

FIGS. 1 and 2 diagrammatically illustrate the device according to the invention.

DETAILED DESCRIPTION OF EMBODIMENTS

The invention relates to a multisection imaging device, which can in particular be an imaging device in X or γ-ray transmission or in γ-ray remission. In order to simplify the following description, the considered example relates to X-ray transmission (X-ray tomography).

Figure 3:
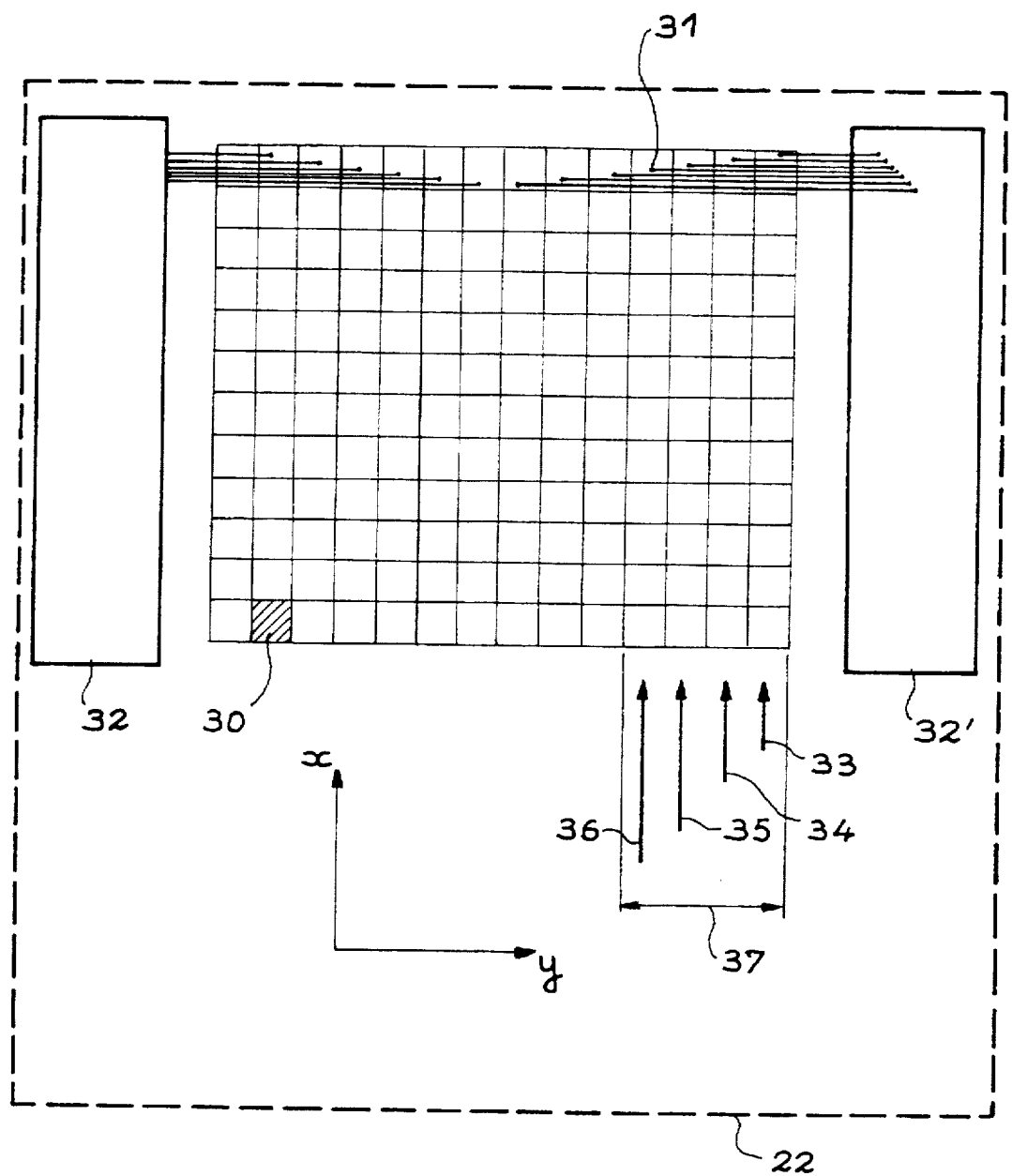
FIG. 3 is the basic diagram of the interconnection of a detector with measuring electronics in the device according to the invention.
Figure 4:
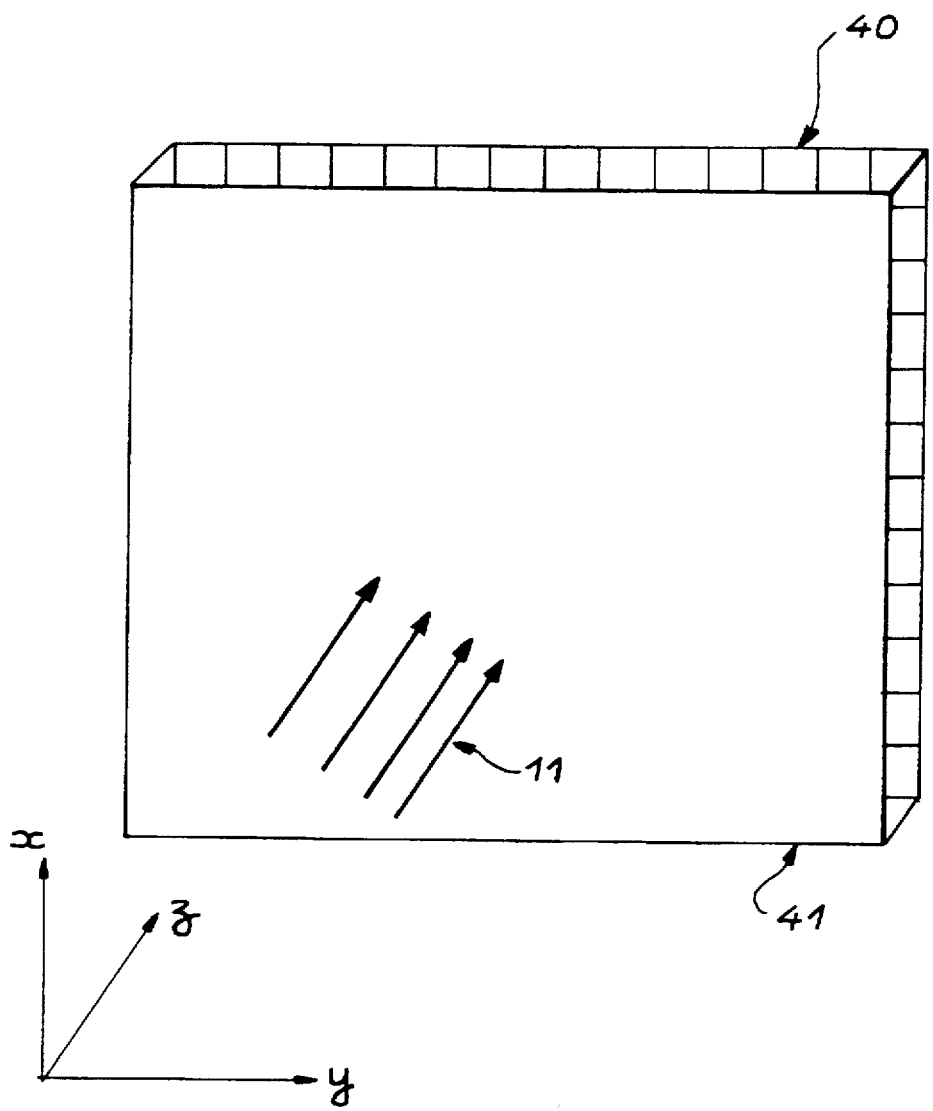
FIG. 4 illustrates the diagram of a semiconductor detector in the device according to the invention.

As shown in FIG. 1, the tomograph according to the invention comprises a source 10 of X radiation 11 and an array of semiconductor detectors 12 rotating 13 about a means 14, which can be an object or a subject (in FIGS. 3 and 4 the means 14 shown is a patient). The thus formed detection ring is constituted by several planar detectors joined together so as to form a continuous array. The planar detectors are arranged in such a way that the perpendicular to each plane (e.g. the z axis) passes through the focus of the X-ray source. The first section is designated 15.

The invention also relates to a tomograph able to acquire measurements according to several sections (advantageously corresponding to the number of rings), which comprises an array of bidimensional (2D) detectors performing a rotary movement about the means 14. Each bidimensional detector is e.g. obtained from high resistivity, elementary semiconductor detectors, which are joined together so as to form two juxtaposed detection rings. Advantageously, each elementary detector is provided with a blocking contact, which is connected to a metal ball, e.g. based on indium, which is itself connected to a reading circuit.

Each semiconductor detector can be made from a material taken from the families of semiconductors of type IV (SiGe), II-VI (ZnS), III-V (GaAs, InP) and II-VII (HgI2):
CdXTe with e.g. X=Zn or nothing
AsXTe with e.g. X=Alu or nothing
BiXOy with e.g. X=Ge, Si X=12, y=1
PbXO with e.g. X=Ti or nothing
XSe with e.g. X=Cd or nothing The invention also relates to a tomographic process using said device which, on the basis of a single X-radiation dose, makes it possible to obtain an acquisition. The section height can be chosen after each acquisition stage at the time of reconstructing the images by summating the contribution of a chosen number of rings permitting the selection of at least one examination volume and/or the variation thereof.

FIG. 2 shows the same device in section. The reading electronics 20 is connected to the semiconductor detector 21 by means of a connection support 22. It is protected against X radiation by an absorbing material shield 23.

As shown in FIG. 3, each elementary detector is constituted by a semiconductor plate or chip having on the irradiated face a homogeneous electrode and on the other facing face a plurality of small independent electrodes. Each small electrode defines the size of a detector pixel 30. It is connected to a metal strip of an interconnection support by the metal ball method, e.g. based on indium 31, or of conductive rubber. This metal strip is connected to a reading electronics 32 (32') offset to the side by the same method.

The reading circuit can be produced in irradiation hardened technology, but its cost is then high. This type of circuit could be preferred in the case where the device has a large number of detection rings.

Advantageously, the reading circuit is offset from the detector array via tracks (one track per elementary detector) and is provided with an X radiation absorbing shield in order to protect the reading circuit. This method means that all the connections can be kept on a pixel width.

The interest of the semiconductor solution is of directly converting the X radiation into electric charges. The collection electrodes of the detector can be connected to a support by the metal ball method, e.g. based on indium (flip-chip). The electronic measuring circuit is also connected to this support by the same method, but is offset so that it is protected against the incident X-ray beam by a metal shield. The support then effects the interconnection between the detector and the reading circuit by metal strips, as shown in FIG. 3.

By interconnecting such planar detectors in ring form, it is possible to produce a large number of sections at the same time. Each section is defined by a pixel on the Y axis. It is possible to modify the section height during acquisition by summating the signals of a certain number of pixels of the Y axis.

The first section 33 is given by the image reconstruction of the pixel response of the first column of all the planar detectors. Acquisition takes place at the same time of the same number of sections as there are columns. The section height is defined by the dimension of the elementary pixel. It can be increased by summating the response of several pixels on a line or row.

FIG. 3 shows the first section 33, second section 34, third section 35 and fourth section 36. FIG. 3 also shows the variable section height 37.

FIG. 4, which is a basic diagram of the semiconductor detector, shows the front face 40, which is a solid layer electrode and the rear face which is a pixelized electrode.

The invention describes the use of semiconductor-based detectors for producing multisection imaging devices, e.g. tomographs, which is made possible by the use of blocking contacts (e.g. aluminium, indium and silver). Such blocking contacts, which are stable in time for an ionizing radiation, e.g. a X radiation, lead to a significant improvement to the detection quality.

Several comparative application examples will be considered. Typically, for locating a given object with a device having a 1 m long, 12 mm wide detector array, which passes round a patient and a collimator for reducing the section width between two experiments, the following stages are involved;

a section width is fixed, e.g. 10 mm,
a certain number of sections, e.g. five is produced in order to inspect a width of 50 mm,
an anomaly appears on a section,
repositioning takes place with respect to the anomaly,
the process is recommenced by reducing the section width e.g. 2 mm and five sections are again produced.

Continuation is possible, but for each section there is an accumulation of the radiation doses at the same location of the body (5 rem on each occasion). This process is also long. It is also difficult to align a large number of detectors on the same array.

However, with the device according to the invention, for a 1000 pixel, 25 mm wide detector, the section width is equal to one pixel, i.e. 250 μm, so that there is one electrode per elementary point and a dead space between two pixels in order to prevent short-circuits:

a rotation is performed,
with a single radiation dose 100 sections are produced for inspecting a 50 mm width, whilst obtaining one information per pixel,
on the basis of the acquired data, it is possible to reconstruct the entire volume on 25 mm in order to have a global vision and/or reconstruct on smaller widths to be chosen.

In other words, with the process according to the invention, in order to expect a volume, whose maximum height corresponds to the height formed by the stack of detector rings, it is possible to proceed in several ways:

it is possible to select one ring or an array of rings in order to produce a high resolution image of the chosen area with the aid of a summation process for the response of the rings, followed by reconstruction,
it is possible to partition or sample the examination area, e.g. there are 100 sections with a spacing of 250 μm,
it is possible to carry out a reconstruction every millimetre with a 250 μm section height, then reconstructing a section every millimetre with a resolution of 1 mm,
a 10 mm high section can be produced.

The invention makes it possible to obtain a better resolution, because the sections can have a height of 250 μm, whereas the prior art devices give wider sections.

One of the advantages of the invention is to solve the positioning problem e.g. relative to a tumour encountered in the prior art devices.

On the basis of measurements obtained with the imaging device according to the invention, the reconstruction of images e.g. takes place in conventional manner on the basis of a projection using a 2D or 3D Radon transform.

REFERENCES

[1] "Development of a 3D CT-Scanner using Cone Beam" by Masahiro Endo, Nozomu Kamagata, Kazumasa Sato, Yuichi Hattori, Shigeo Kobayaghi, Shin-Ichi Mizuno, Masao Jimbo and Masahiro Kusakabe (SPIE, vol. 2432, pages 291 to 297)

[2] "New CT Scanner—Initial Clinical Experience" by C. Becker, U. Fink, M. Seemann and M. Reiser (Electromedica 63; 1995; No. 1)

[3] FR-A-2 432 718; "Radiation detection device for tomography" by "The Regents of the University of California", Mar. 26, 1979

[4] EP-A-0 571 135; "Hybridized Semiconductor Pixel Detector Arrays for use in Digital Radiography" by Timothy Collins, Stuart Worley, Gordon Kramer and W. Douglas Wolfe; 13 May 1993

We claim:

1. Multisection imaging device comprising an ionizing radiation source having a focus and an array of bidimensional semiconductor detectors each adapted to receive said radiation along an associated axis perpendicular thereto after the radiation has traversed a means, said bidimensional semiconductor detectors being planar, joined together so as to form a continuous array, arranged in such a way that the perpendicular axis to each of them passes through the focus of the source, and being formed of elementary semiconductor detectors joined together, so as to provide several detection rings able to rotate about said means in order to permit the simultaneous acquisition of several imaging sections, wherein each elementary semiconductor detector is provided with a blocking contact.

2. Device according to claim 1, wherein the ionizing radiation source is a X-ray source.

3. Device according to claim 1, wherein the ionizing radiation source is a γ-ray source.

4. Device according to claim 1, wherein each elementary semiconductor detector is a high resistivity detector.

5. Device according to claim 4, wherein each semiconductor detector is made from a material taken from within the semiconductor families of type IV (SiGe), II-VI (ZnS), III-V (GaAs, Inp), II-VII (HgI2).

6. Device according to claim 1 having a reading circuit protected from the incident beam received from the ionizing radiation source by means of a connection support.

7. Device according to claim 6, wherein the elementary semiconductor detectors and the reading circuit are connected to said support by metal bumps.

8. Device according to claim 6, wherein the reading circuit is connected to the semiconductor detectors by means of a connection support and wherein said reading circuit is protected from the radiation by an absorbing material shield.

9. Device according to claim 1, wherein each elementary semiconductor is constituted by a semiconductor plate or chip having on a face irradiated by the ionizing radiation a homogenous electrode and on another facing face a plurality of small independent electrodes, each small electrode defining the size of a detector pixel.

10. Device according to claim 9, wherein each small electrode is connected to a metal strip of an interconnection support by means of metal bumps.

11. Device according to claim 10, wherein said metal strip is connected to the reading circuit, which is offset to the side by means of indium bumps.

12. Device according to claim 1, wherein the said means is an object.

13. Device according to claim 1, wherein said means is a patient.

14. Imaging process performed by a multisection imaging device incorporating an ionizing radiation source having a focus and an array of bidimensional semiconductor detectors each adapted to receive said radiation which has traversed a means, said bidimensional semiconductor detectors being planar, being joined together so as to form a continuous array, being arranged in such a way that the perpendicular to each of them passes through the focus of the source, and being formed of elementary semiconductor detectors joined together, so as to provide several detection rings able to rotate about the means in order to permit the simultaneous acquisition of several imaging sections, wherein, on the basis of a single ionizing radiation dose making it possible to carry out an acquisition, the section height can be chosen following the acquisition stage, at the time of reconstructing images, by summing the contribution of a chosen number of rings, permitting the selection of at least one examination volume and/or the variation thereof.

15. Process according to claim 14, wherein a first section is given by the reconstruction of images of the response of pixels of the first column of all the planar detectors and wherein acquisition takes place at the same time of the same number of sections as there are columns, the section height being defined by the dimension of the elementary pixel.

16. Process according to claim 15, wherein the section height is increased during acquisition by summing the response of several pixels on a line.

* * * * *